United States Patent
Yi et al.

(10) Patent No.: US 10,826,124 B2
(45) Date of Patent: *Nov. 3, 2020

(54) ELECTROLYTE AND ELECTROCHEMICAL DEVICE

(71) Applicant: Contemporary Amperex Technology Co., Limited, Ningde, Fujian Province (CN)

(72) Inventors: Tiancheng Yi, Ningde (CN); Chunhua Hu, Ningde (CN); Yao Jiang, Ningde (CN); Lu Miao, Ningde (CN); Chengdu Liang, Ningde (CN)

(73) Assignee: Contemporary Amperex Technology Co., Ltd., Ningde (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/388,216

(22) PCT Filed: Jul. 18, 2017

(86) PCT No.: PCT/CN2017/093306
§ 371 (c)(1),
(2) Date: Apr. 18, 2019

(87) PCT Pub. No.: WO2019/010719
PCT Pub. Date: Jan. 17, 2019

(65) Prior Publication Data
US 2020/0127330 A1   Apr. 23, 2020

(30) Foreign Application Priority Data
Jul. 14, 2017 (CN) .......................... 2017 1 0574732

(51) Int. Cl.
H01M 10/0525 (2010.01)
H01M 10/0567 (2010.01)
(Continued)

(52) U.S. Cl.
CPC ...... H01M 10/0567 (2013.01); C07D 239/04 (2013.01); C07D 241/04 (2013.01);
(Continued)

(58) Field of Classification Search
CPC ......... H01M 10/0567; H01M 10/0525; H01M 6/16; H01M 2300/0025; C07D 239/04;
(Continued)

(56) References Cited

U.S. PATENT DOCUMENTS

| | | | | |
|---|---|---|---|---|
| 2015/0064578 A1* | 3/2015 | Kang | ................ | H01M 10/0567 429/341 |
| 2015/0152045 A1* | 6/2015 | Schmidt | ............ | H01M 10/0567 429/338 |
| 2015/0364794 A1 | 12/2015 | Nakazawa et al. | | |

FOREIGN PATENT DOCUMENTS

| CN | 105789703 A | 7/2016 |
|---|---|---|
| CN | 105845981 A | 8/2016 |

(Continued)

OTHER PUBLICATIONS

Supplemental material (Year: 2014).*
International Search Report.
(Continued)

Primary Examiner — Alexander Usyatinsky
(74) Attorney, Agent, or Firm — Panagos Kennedy PLLC; Bill Panagos; Linda Kennedy

(57) ABSTRACT

An electrolyte and an electrochemical device, which relates to the field of energy storage materials. The electrolyte includes an additive A, an additive B and an additive C, the additive A selected from a group consisting of multi-cyano six-membered N-heterocyclic compounds represented by Formula I-1, Formula I-2 or Formula I-3, and combinations thereof, the additive B is at least one sulfonate compound, and the additive C is at least one halogenated cyclic carbonate compound. The electrochemical device includes the above electrolyte. The electrolyte of the present disclosure can effectively passivate the surface activity of the positive electrode material, inhibit the oxidation of the electrolyte, and effectively reduce gas production of a battery, meanwhile the electrolyte can be also adsorbed catalytically active of the graphite surface to form a more stable SEI film, thereby effectively reducing side reactions

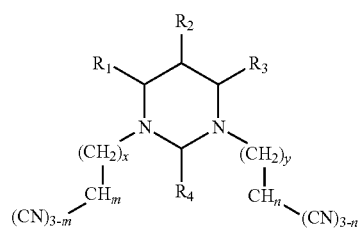

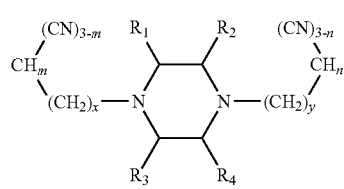

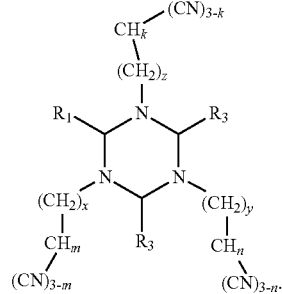

17 Claims, 1 Drawing Sheet

(51) Int. Cl.
  *C07D 239/04* (2006.01)
  *C07D 241/04* (2006.01)
  *C07D 251/04* (2006.01)
  *C07D 317/34* (2006.01)
  *C07D 327/04* (2006.01)
  *H01G 11/06* (2013.01)
  *H01G 11/64* (2013.01)
  *H01M 6/16* (2006.01)

(52) U.S. Cl.
  CPC ......... *C07D 251/04* (2013.01); *C07D 317/34* (2013.01); *C07D 327/04* (2013.01); *H01G 11/06* (2013.01); *H01G 11/64* (2013.01); *H01M 6/168* (2013.01); *H01M 10/0525* (2013.01); *H01M 2300/0025* (2013.01)

(58) Field of Classification Search
  CPC .. C07D 241/04; C07D 251/04; C07D 317/34; C07D 327/04; H01G 11/06; H01G 11/64
  See application file for complete search history.

(56) References Cited

FOREIGN PATENT DOCUMENTS

| | | | |
|---|---|---|---|
| CN | 106340670 A | | 1/2017 |
| EP | 3471191 | * | 4/2017 |
| JP | 2012212516 A | | 11/2012 |
| WO | WO2009132740 | | 11/2009 |
| WO | WO2016159702 | | 10/2016 |

OTHER PUBLICATIONS

European Search Report for App. No. 17917531.0.
Chinese Office Action for App. No. 201710574732.5.
Japanese Reasons for Refusal for App. No. 2019-516201.

* cited by examiner

ELECTROLYTE AND ELECTROCHEMICAL DEVICE

CROSS-REFERENCE TO RELATED APPLICATIONS

The present application is based on International Application No. PCT/CN2017/093306, filed on Jul. 18, 2017, which claims priority to Chinese Patent Application No. 201710574732.5, filed on Jul. 14, 2017, the contents of which are incorporated herein by reference in their entireties.

TECHNICAL FIELD

The present disclosure relates to the field of energy storage materials, and particularly, to an electrolyte and an electrochemical device.

BACKGROUND

Lithium-ion batteries are widely used in electric vehicles and consumer electronic products due to their advantages of high energy density, high output power, long cycle life and small environmental pollution. The current demand on lithium-ion batteries still includes: high voltage, high power, long cycle life, long storage life and excellent safety performance.

Most of the current lithium-ion batteries apply an electrolyte system, in which lithium hexafluorophosphate is used as conductive lithium salt and a cyclic carbonate and/or a chain carbonate is used as solvent. However, the above electrolyte system still has many deficiencies. For example, the cycle performance and storage performance of the above electrolyte system need to be improved under a condition of high voltage and high temperature.

The present disclosure aims to overcome the said deficiencies.

SUMMARY

In order to solve the above problems, the inventor conducted intensive researches and found that using a multi-cyano six-membered N-heterocyclic compound and a sulfonate compound together as additives of the electrolyte can effectively inactivate the surface of a positive electrode material, inhibit the positive electrode material from oxidizing the electrolyte, and effectively reduce gas production of the battery, meanwhile the additives can be adsorbed on catalytically active sites of the graphite surface to form a more stable SEI film, thereby significantly reducing side reactions. In this way, the cycle performance at high temperature and high voltage and the storage performance of the battery can be improved. The present application is completed based on the above concept.

One purpose of the present disclosure is to provide an electrolyte including an additive A, an additive B and an additive C.

The additive A is selected from a group consisting of multi-cyano six-membered N-heterocyclic compounds represented by Formula I-1, Formula I-2 and Formula I-3, and combinations thereof:

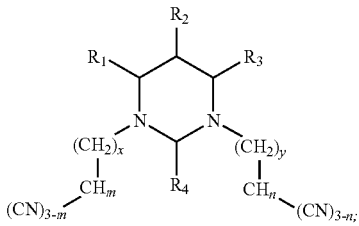
(I-1)

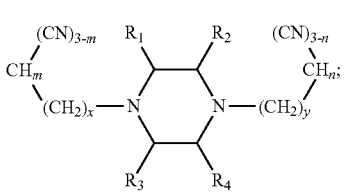
(I-2)

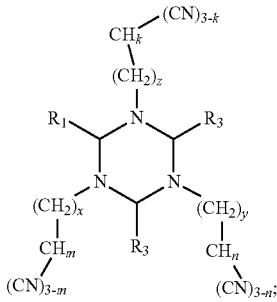
(I-3)

wherein $R_1$, $R_2$, $R_3$ and $R_4$ are each independently selected from a group consisting of hydrogen, halogen, substituted or unsubstituted $C_1$-$C_{12}$ alkyl, substituted or unsubstituted $C_1$-$C_{12}$ alkoxy, substituted or unsubstituted $C_1$-$C_{12}$ amine group, substituted or unsubstituted $C_2$-$C_{12}$ alkenyl, substituted or unsubstituted $C_2$-$C_{12}$ alkynyl, substituted or unsubstituted $C_6$-$C_{26}$ aryl, and substituted or unsubstituted $C_4$-$C_{12}$ heterocyclic group;

the substituent for the above groups, if present, is independently selected from a group consisting of halogen, cyano, $C_1$-$C_6$ alkyl, $C_2$-$C_6$ alkenyl, $C_1$-$C_6$ alkoxy, and combinations thereof;

x, y and z are each an integer independently selected from 0-8; and m, n and k are each an integer independently selected from 0-2; preferably, m, n and k are each independently 1 or 2;

wherein the additive B is at least one sulfonate compound; and the additive C is at least one halogenated cyclic carbonate compound.

Another purpose of the present disclosure is to provide an electrochemical device including a positive electrode plate, a negative electrode plate, a separator positioned between the positive electrode plate and the negative electrode plate, and an electrolyte according to the present disclosure.

The technical solutions of the present disclosure at least have the following beneficial effects:

The addition of both the multi-cyano six-membered N-heterocyclic compound and the sulfonate compound as additives of the electrolyte according to the present disclosure can effectively passivate surface activity of the positive electrode material, inhibit the positive electrode material from oxidizing the electrolyte, and effectively reduce gas production of the battery, meanwhile the additives can be adsorbed on catalytically active sites of the graphite surface to form a more stable SEI film, thereby effectively reducing reductive decomposition of the electrolyte and effectively reducing side reactions.

The electrochemical device using the electrolyte according to the present disclosure has a good cycle performance at high temperature and high voltage and a good storage performance.

DESCRIPTION OF EMBODIMENTS

Figure 1:
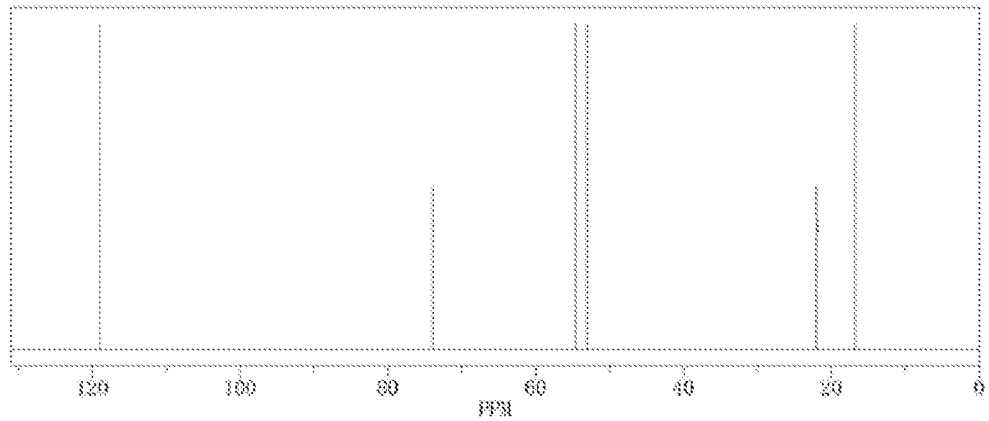
FIG. 1 is a nuclear magnetic resonance carbon spectrum of Compound A2.

In order to clarify invention purpose, technical solutions, and advantages of the present disclosure, the present disclosure will be described in detail below with reference to the embodiments. It should be understood that the embodiments described in the specification merely aim to explain the present disclosure, rather than limiting the present disclosure. Formulations, ratios, etc. mentioned in the embodiments can be selected depending upon actual conditions and requirements.

The electrolyte and battery according to the present application are described in detail below.

Firstly, according to a first aspect of the present disclosure, an electrolyte is described as below. The electrolyte according to the present disclosure can be a liquid electrolyte or a solid electrolyte. The electrolyte is embodied as the liquid electrolyte to illustrate the present disclosure.

The electrolyte according to the first aspect of the present disclosure includes an organic solvent, an electrolyte salt, and an additive. The additive includes an additive A, an additive B and an additive C. The additive A is at least one multi-cyano six-membered N-heterocyclic compound, the additive B is at least one sulfonate compound, and the additive C is at least one halogenated cyclic carbonate compound.

(Additive A)

The additive A is selected from a group consisting of multi-cyano six-membered N-heterocyclic compounds represented by Formula I-1, Formula I-2 and Formula I-3, and combinations thereof:

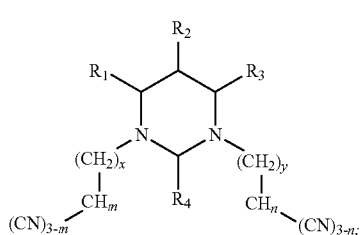
(I-1)

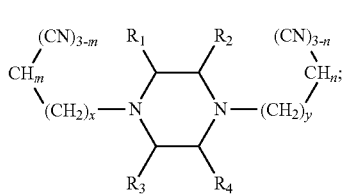
(I-2)

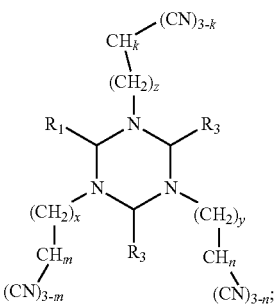
(I-3)

in which $R_1$, $R_2$, $R_3$ and $R_4$ are each independently selected from a group consisting of hydrogen, halogen, substituted or unsubstituted $C_1$-$C_{12}$ alkyl, substituted or unsubstituted $C_1$-$C_{12}$ alkoxy, substituted or unsubstituted $C_1$-$C_{12}$ amine group, substituted or unsubstituted $C_2$-$C_{12}$ alkenyl, substituted or unsubstituted $C_2$-$C_{12}$ alkynyl, substituted or unsubstituted $C_6$-$C_{26}$ aryl, and substituted or unsubstituted $C_4$-$C_{12}$ heterocyclic group;

the substituent for the above groups, if present, is independently selected from a group consisting of halogen, cyano, $C_1$-$C_6$ alkyl, $C_2$-$C_6$ alkenyl, $C_1$-$C_6$ alkoxy, and combinations thereof;

x, y and z are each an integer independently selected from 0-8; and m, n and k are each an integer independently selected from 0-2.

Since the multi-cyano six-membered N-heterocyclic compound have cyano groups and the nitrogen atoms in the cynao groups can be strongly complexed with transition metals, the multi-cyano six-membered N-heterocyclic compound applied in the electrolyte can be adsorbed on the surface of the positive electrode material to form a loose porous protective film. The porous protective film isolates the surface of the positive electrode material from the electrolyte without affecting normal transportation of lithium ions, reduces the surface activity of the positive electrode material, and meanwhile inhibits a large number of side reactions occurring on the surface, thereby reducing by-products and inhibiting gas production.

Further, although the multi-cyano six-membered N-heterocyclic compound according to the present disclosure is a nitrile-derived compound, a special six-membered N-heterocyclic structure thereof can affect a film forming potential of the cynao group and a film forming effect on the surface of the positive electrode material, and further can improve electrochemical performance of the entire battery system, such as reducing gas production, increasing cycle life at high temperature and high voltage, etc.

(I) In the embodiments of the present application, the compounds represented by Formula I-1 are multi-cyano pyrimidine compounds.

As an improvement of the compounds represented by Formula I-1, $R_1$, $R_2$, $R_3$ and $R_4$ are each independently selected from a group consisting of hydrogen, halogen, substituted or unsubstituted $C_1$-$C_6$ linear or branched alkyl, substituted or unsubstituted $C_5$-$C_9$ cycloalkyl, substituted or unsubstituted $C_1$-$C_6$ alkoxy, substituted or unsubstituted $C_1$-$C_6$ amine group, substituted or unsubstituted $C_2$-$C_6$ alkenyl, substituted or unsubstituted $C_2$-$C_6$ alkynyl, substituted or unsubstituted $C_6$-$C_{12}$ aryl, and substituted or unsubstituted $C_4$-$C_{12}$ heterocyclic group. The substituent for the above groups, if present, is halogen.

As an improvement of the compounds represented by Formula I-1, $R_1$, $R_2$, $R_3$ and $R_4$ each are independently selected from a group consisting of hydrogen, halogen, substituted or unsubstituted $C_1$-$C_3$ linear or branched alkyl, substituted or unsubstituted $C_5$-$C_7$ cycloalkyl, substituted or unsubstituted $C_1$-$C_3$ alkoxy, substituted or unsubstituted $C_1$-$C_3$ amine group, substituted or unsubstituted $C_2$-$C_3$ alkenyl, substituted or unsubstituted $C_2$-$C_3$ alkynyl, substituted or unsubstituted $C_6$-$C_8$ aryl, and substituted or unsubstituted $C_4$-$C_7$ heterocyclic group. The substituent group for the above groups, if present, is halogen.

Each of alkyl, alkenyl and alkynyl can be a chain substituent or a cyclic substituent, and the chain substituent can be either a linear substituent or a branched substituent.

In the compounds represented by Formula I-1, x is preferably an integer selected from 0-6, further preferably an integer selected from 0-4, more preferably 1 or 2; and y is preferably an integer selected from 0-6, further preferably an integer selected from 0-4, more preferably 1 or 2.

As an improvement of the compounds represented by Formula I-1, $R_1$ and $R_3$ are identical; optionally, $R_1$, $R_3$ and $R_4$ are identical.

As an improvement of the compounds represented by Formula I-1, both $R_1$ and $R_3$ are hydrogen; optionally, $R_1$, $R_3$ and $R_4$ are hydrogen.

As an improvement of the compounds represented by Formula I-1, $R_1$ to $R_4$ all are hydrogen; or $R_1$, $R_3$ and $R_4$ are hydrogen, $R_2$ is selected from a group consisting of halogen, substituted or unsubstituted $C_1$-$C_6$ linear or branched alkyl, and substituted or unsubstituted $C_1$-$C_6$ alkoxy; and the substituent for the above groups, if present, is halogen, preferably fluorine.

As an improvement of the compounds represented by Formula I-1, the compounds represented by Formula I-1 are selected from, but not limited to, a group consisting of the following compounds:

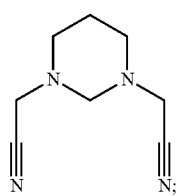
(A1)

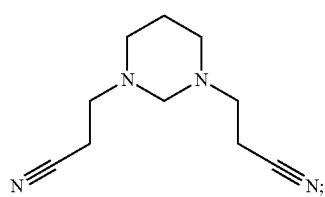
(A2)

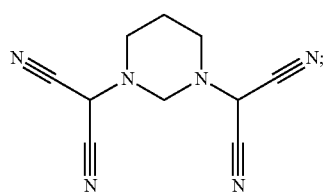
(A3)

-continued

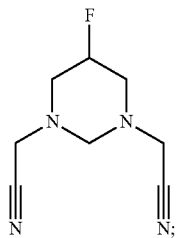
(A4)

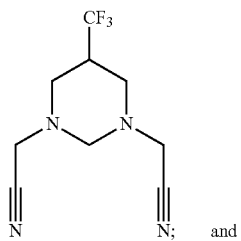
(A5)

and

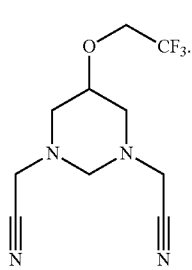
(A6)

(II) In the embodiments of the present disclosure, the compounds represented by Formula I-2 are multi-cyano piperazine compounds.

As an improvement of the compounds represented by Formula I-2, $R_1$, $R_2$, $R_3$ and $R_4$ each are independently selected from a group consisting of hydrogen, halogen, substituted or unsubstituted $C_1$-$C_6$ linear or branched alkyl, substituted or unsubstituted $C_5$-$C_9$ cycloalkyl, substituted or unsubstituted $C_1$-$C_6$ alkoxy, substituted or unsubstituted $C_1$-$C_6$ amine group, substituted or unsubstituted $C_2$-$C_6$ alkenyl, substituted or unsubstituted $C_2$-$C_6$ alkynyl, substituted or unsubstituted $C_6$-$C_{12}$ aryl, and substituted or unsubstituted $C_4$-$C_{13}$ heterocyclic group; and a substituent for the above groups, if present, is halogen.

As an improvement of the compounds represented by Formula I-2, $R_1$, $R_2$, $R_3$ and $R_4$ each are independently selected from a group consisting of hydrogen, halogen, substituted or unsubstituted $C_1$-$C_3$ linear or branched alkyl, substituted or unsubstituted $C_5$-$C_7$ cycloalkyl, substituted or unsubstituted $C_1$-$C_3$ alkoxy, substituted or unsubstituted $C_1$-$C_3$ amine group, substituted or unsubstituted $C_2$-$C_3$ alkenyl, substituted or unsubstituted $C_2$-$C_3$ alkynyl, substituted or unsubstituted $C_6$-$C_8$ aryl, and substituted or unsubstituted $C_4$-$C_7$ heterocyclic group; and the substituent for the above groups, if present, is halogen.

Each of alkyl, alkenyl and alkynyl can be a chain substituent or a cyclic substituent, and the chain substituent can be either a linear substituent or a branched substituent.

In the compounds represented by Formula I-2, x is preferably an integer selected from 0-6, further preferably an integer selected from 0-4, more preferably 1 or 2; and y is preferably an integer selected from 0-6, further preferably an integer selected from 0-4, more preferably 1 or 2.

As an improvement of the compounds represented by Formula I-2, at least two of $R_1$, $R_2$, $R_3$ and $R_4$ are identical; and optionally, at least three of $R_1$, $R_2$, $R_3$ and $R_4$ are identical.

As an improvement of the compounds represented by Formula I-2, at least two of $R_1$, $R_2$, $R_3$ and $R_4$ are hydrogen; and optionally, at least three of $R_1$, $R_2$, $R_3$ and $R_4$ are hydrogen.

As an improvement of the compounds represented by Formula I-2, $R_1$ to $R_4$ all are hydrogen; or at least three of $R_1$, $R_2$, $R_3$ and $R_4$ are hydrogen and the remaining one of $R_1$, $R_2$, $R_3$ and $R_4$ is selected from a group consisting of halogen, substituted or unsubstituted $C_1$-$C_6$ linear or branched alkyl, and substituted or unsubstituted $C_1$-$C_6$ alkoxy; and the substituent for the above groups, if present, is halogen, and preferably fluorine.

As an improvement of the compounds represented by Formula I-2, the compounds represented by Formula I-2 are selected from, but not limited to, a group consisting of the following compounds:

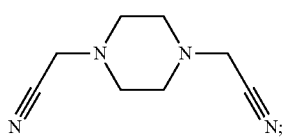
(A7)

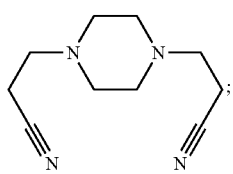
(A8)

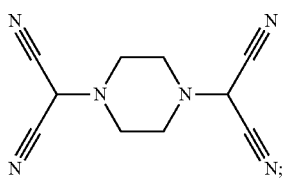
(A9)

cent of the electrolyte in the embodiments of the present disclosure, the additive A is 0.001% to 10% by weight of the electrolyte. If the content of the additive A is too low, the improvement effect on the electrolyte will be not significant. If the content of the additive A is too high, a complex layer to be formed will have a great thickness, which significantly increases impedances of the positive and negative electrodes and thus leads to a deterioration of battery performance.

In the embodiments of the present disclosure, the additive A is at most 10%, 9%, 8%, 7%, 6%, 5%, 4.5%, 4%, 3.5%, 3%, 2%, 1.5%, 1.2% or 1.0%, by weight of the electrolyte, and at least 0.001%, 0.005%, 0.01%, 0.05%, 0.1%, 0.3%, 0.5%, 0.6%, 0.8%, or 0.9%, by weight of the electrolyte.

Preferably, the additive A is 0.01% to 6%, preferably 0.1% to 3.5% by weight of the electrolyte.

(Additive B)

The sulfonate compound, as the additive B, can be selected from a group consisting of a group consisting of a sultone compound, a disulfonate compound, and combinations thereof. The additive B has a relatively high reduction potential, and thus can be preferentially reduced on the graphite electrode surface. The reduction product containing sulfur element is adsorbed on catalytically active sites of the graphite surface to form a more stable SEI film, thereby effectively reducing the reductive decomposition of the electrolyte and reducing the side reactions.

Specifically, the sultone compound is at least one of compounds represented by Formula II-1,

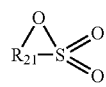
(II-1)

in which $R_{21}$ is selected from substituted or unsubstituted $C_1$-$C_6$ alkylene, and substituted or unsubstituted $C_2$-$C_6$ alkenylene, where the substituent for the above groups, if present, is halogen, $C_1$-$C_3$ alkyl, or $C_2$-$C_4$ alkenyl.

Further optionally, $R_{21}$ is selected from substituted or unsubstituted $C_1$-$C_4$ alkylene, and substituted or unsubstituted $C_2$-$C_4$ alkenylene, where the substituent for the above groups, if present, is halogen, $C_1$-$C_3$ alkyl, or $C_2$-$C_4$ alkenyl.

Specifically, the sultone compound is selected from 1,3-propane sultone (abbreviated as PS), 1,3-propene sultone (abbreviated as PES), and combinations thereof. Structural formulas of PS and PES are shown as follows:

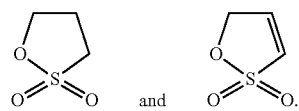 [SMILES: O=S1(=O)CCCO1 ; "and" ; O=S1(=O)C=CCO1]

Specifically, the disulfonate compound is at least one of compounds represented by Formula II-2,

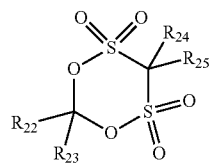
(II-2)

in which $R_{22}$, $R_{23}$, $R_{24}$ and $R_{25}$ are each independently selected from hydrogen, halogen, substituted or unsubstituted $C_1$-$C_{10}$ alkyl, and substituted or unsubstituted $C_2$-$C_{10}$ alkenyl, where the substituent for the above groups, if present, is halogen, $C_1$-$C_3$ alkyl, or $C_2$-$C_4$ alkenyl.

Further optionally, $R_{22}$, $R_{23}$, $R_{24}$ and $R_{25}$ are each independently selected from hydrogen, halogen, substituted or unsubstituted $C_1$-$C_6$ alkyl, and substituted or unsubstituted $C_2$-$C_6$ alkenyl, where the substituent for the above groups, if present, is halogen, $C_1$-$C_3$ alkyl, or $C_2$-$C_4$ alkenyl.

Methylene disulfonate compound can be methylene methanedisulfonate (abbreviated as MMDS):

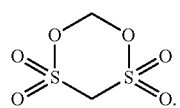

The methylene disulfonate compound can also be selected from a group consisting of 3-methyl-methylene methanedisulfonate, compounds having the following structures, and combinations thereof:

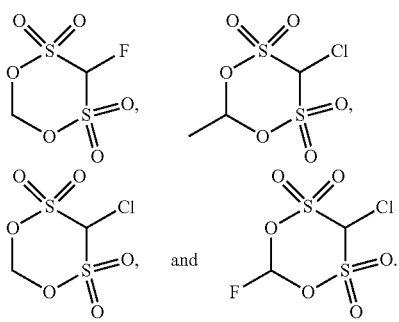
and

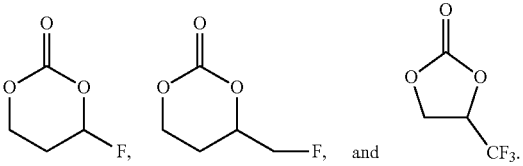

As an improvement of the electrolyte in the embodiments of the present disclosure, the additive B is 0.1% to 10% by weight of the electrolyte. If the content of the additive B is too low, the improvement effect on the electrolyte will be not significant. If the content of the additive B is too high, the formed SEI film will have a great thickness, which adversely affects a cycle capacitance retention rate of the battery and thus deteriorates battery performance In the embodiments of the present disclosure, the additive B is at most 10%, 9%, 8%, 7%, 6%, 5%, 4.5%, 4%, 3.5%, 3%, 2%, or 1.8%, by weight of the electrolyte, and at least 0.1%, 0.25%, 0.25%, 0.3%, 0.5%, 0.6%, 0.8%, 0.9%, 1.0%, 1.2%, or 1.5%, by weight of the electrolyte.

Further, the additive B is 0.5% to 7%, preferably 1% to 4% by weight of the electrolyte.

(Additive C)

Other additive, as an additive C, can be further added to the electrolyte according to the embodiments of the present disclosure. Specifically, the additive C can be selected from halogenated cyclic carbonate compounds. The unsaturated bond in the additive C is conducive to forming a dense negative electrode SEI film, which prevents a contact between the negative electrode and the electrolyte, thereby significantly reducing side reactions.

Specifically, the halogenated cyclic carbonate compound is selected from a group consisting of compounds represented by Formula III and combinations thereof:

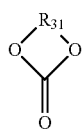 (III)

in which $R_{31}$ is selected from halogenated $C_1$-$C_6$ alkylene, and halogenated $C_2$-$C_6$ alkenylene.

Further optionally, $R_{31}$ is selected from halogenated $C_1$-$C_4$ alkylene, and halogenated $C_2$-$C_4$ alkenylene.

The halogenated cyclic carbonate compound is selected a group consisting of the following compounds and combinations thereof:

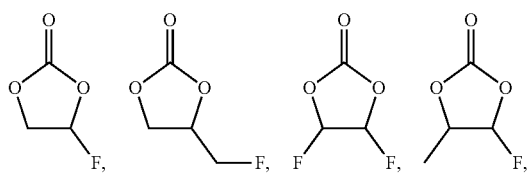

-continued

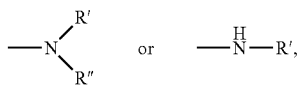

As an improvement of the electrolyte of the embodiments of the present disclosure, the additive C is 0.1% to 10% by weight of the electrolyte. If the content of additive C is too low, the improvement effect of additive C on the electrolyte will be not significant. If the content of the additive C is too high, the formed SEI film will be too thick, which adversely affects the cycle capacitance retention rate of the battery and negatively affects the performance of the battery.

In the embodiments of the present disclosure, the additive C is at most 10%, 9%, 8%, 7%, 6%, 5%, 4.5%, 4%, 3.5%, 3%, 2%, or 1.8%, by weight of the electrolyte, and at least 0.1%, 0.2%, 0.25%, 0.3%, 0.5%, 0.6%, 0.8%, 0.9%, 1.0%, 1.2%, or 1.5%, by weight of the electrolyte.

Further preferably, the additive C is 0.5% to 6%, more preferably 1% to 4% by weight of the electrolyte.

In the Formula I-1, Formula I-2, and Formula I-3 in the embodiments of the present disclosure:

$C_1$-$C_{12}$ alkyl is alkyl having 1 to 12 carbon atoms, and can be a chain alkyl or a cycloalkyl; hydrogen on a ring of cycloalkyl can be substituted by alkyl; a preferable lower limit of a number of carbon atoms of alkyl is 1, 2, 3, 4, or 5; and a preferable upper limit of the number of carbon atoms of alkyl is 3, 4, 5, 6, 8, 10, or 12. Preferably, alkyl having 1-10 carbon atoms is selected; more preferably, a chain alkyl having 1-6 carbon atoms or a cycloalkyl having 3-8 carbon atoms is selected; and most preferably, a chain alkyl having 1-4 carbon atoms or a cycloalkyl having 5-7 carbon atoms is selected. Examples of alkyl include: methyl, ethyl, n-propyl, iso-propyl, n-butyl, iso-butyl, sec-butyl, tert-butyl, n-amyl, iso-amyl, neo-amyl, hexyl, 2-methyl-amyl, 3-methyl-amyl, 1,1,2-trimethylpropyl, 3,3,-dimethyl-butyl, heptyl, 2-heptyl, 3-heptyl, 2-methylhexyl, 3-methylhexyl, iso-heptyl, octyl, nonyl, and decyl.

Alkoxy is the above-mentioned alkyl having 1-12 carbon atoms and having oxygen atom. Preferably, alkoxy having 1-10 carbon atoms is selected; more preferably, alkoxy having 1-6 carbon atom is selected; and most preferably, alkoxy having 1-4 carbon atoms is selected. Examples of alkoxy can include: methoxyl, ethoxy, propyloxy, iso-propoxy, butoxy, sec-butoxy, tert-butoxy, pentyloxy, iso-pentyloxy, cyclopentyloxy, and cyclohexyloxy.

$C_2$-$C_{12}$ alkenyl is alkenyl having 2-12 carbon atoms, and can be a cyclic alkenyl or a chain alkenyl. The alkenyl preferably contains only one double-bond. A preferable lower limit of a number of carbon atoms of alkenyl is 3, 4, or 5, and a preferable upper limit thereof is 3, 4, 5, 6, 8, 10, or 12. Preferably, alkenyl containing 2-10 carbon atoms is selected; more preferably, alkenyl containing 2-6 carbon atoms is selected; and most preferably, alkenyl containing 2-5 carbon atoms is selected. Examples of the alkenyl include: vinyl, allyl, isopropenyl, pentenyl, cyclohexenyl, cycloheptenyl, and cyclooctenyl.

$C_1$-$C_{12}$ amine group is amine group having 1-12 carbon atoms, and is $$-N\begin{subarray}{l}R'\\R''\end{subarray} \quad \text{or} \quad -\overset{H}{N}-R',$$

where R' and R" are each independently alkyl containing 1-12 carbon atoms.

$C_2$-$C_{12}$ alkynyl is alkynyl having 2-12 atoms, and can be a cyclic alkynyl or a chain alkynyl. Alkynyl preferably contains only one triple bond. A preferable lower limit of a number of carbon atoms of alkynyl is 3, 4, or 5, and a preferable upper limit thereof is 3, 4, 5, 6, 8, 10, or 12. Preferably, alkynyl containing 2-10 carbon atoms is selected; more preferably, alkynyl containing 2-6 carbon atoms; and most preferably, alkynyl containing 2-5 carbon atoms is selected. Examples of the alkenyl include: acetenyl, propargyl, isopropynyl, pentynyl.

$C_6$-$C_{26}$ aryl is aryl having 6-26 carbon atoms, for example, phenyl, phenylalkyl, aryl containing at least one phenyl such as biphenyl, and polycyclic aryl such as naphthyl, anthryl, and phenanthryl; the biphenyl and the polycyclic aryl can be substituted by alkyl or alkenyl. Preferably, aryl having 6-16 carbon atoms is selected; more preferably, aryl containing 6-14 carbon atoms is selected; and most preferably, an aryl containing 6-9 carbon atoms is selected. Examples of the aryl include: phenyl, benzyl, biphenyl, p-tolyl, o-tolyl, m-tolyl.

$C_4$-$C_{12}$ heterocyclic group is a heterocyclic group containing having 4-12 carbon atoms, a heteroatom thereof can be oxygen, nitrogen, sulfur, phosphorus, boron, etc.; and a heterocyclic ring thereof can be a hetero alicyclic ring or a hetero aromatic ring, and can be a five-membered or six-membered heterocyclic ring or a benzoheterocyclic ring. Preferably, a heterocyclic group having 4-10 carbon atoms is selected; and more preferably, a heterocyclic group having 4-7 carbon atoms is selected. Specific examples include: furyl, thienyl, pyrrolyl, thiazolyl, imidazolyl, pyridyl, pyrazinyl, pyrimidyl, pyridazinyl, indolyl, quinolyl, etc.

Halogen is fluorine, chlorine, or bromine, and fluorine is preferable.

In the Formula II-1, Formula II-2, and Formula III in the embodiments of the present disclosure:

$C_1$-$C_6$ alkylene is a linear or branched alkylene having 1-6 carbon atoms; a preferable lower limit of a number of carbon atoms of alkylene is 2 or 3, and a preferable upper limit thereof is 4, 5, or 6. Preferably, alkylene having 1-4 carbon atoms is selected. Examples of alkyl include methylene, ethylene, propylidene, iso-propylidene, butylidene, iso-butylidene, sec-butylidene, pentylidene, hexylidene.

$C_2$-$C_6$ alkenylene is a linear or branched alkenylene having 2-6 carbon atoms, and preferably contains only one double bond. A preferable lower limit of a number of carbon atoms of alkenylene is 3 or 4, and a preferable upper limit thereof is 3, 4, 5, or 6. Preferably, alkenylene containing 2-5 carbon atoms is selected. Examples of the alkenylene include: vinylidene, propylidene, isopropylidene, butenylidene, and pentenylidene.

$C_1$-$C_{10}$ alkyl is alkyl having 1 to 10 carbon atoms, and can be a chain alkyl or a cycloalkyl. Hydrogen on a ring of cycloalkyl can be substituted by alkyl. A preferable lower limit of a number of carbon atoms of alkyl having 1 to 10 carbon atoms can be 1, 2, 3, or 4, and a preferable upper limit of the number of carbon atoms thereof is 3, 4, 5, 6, or 8. Preferably, alkyl having 1-6 carbon atoms is selected; more preferably, a chain alkyl having 1-6 carbon atoms or a cycloalkyl having 3-8 carbon atoms is selected; and most preferably, a chain alkyl having 1-4 carbon atoms or a cycloalkyl having 5-7 carbon atoms is selected.

$C_2$-$C_{10}$ alkenyl is alkenyl containing 2-10 carbon atoms, and can be a cyclic alkenyl or a chain alkenyl. The alkenyl preferably contains only one double-bond. A preferable lower limit of a number of carbon atoms of alkenyl is 3, 4, or 5, and a preferable upper limit thereof is 3, 4, 5, 6, or 8. Preferably, alkenyl containing 2-8 carbon atoms is selected; more preferably, alkenyl containing 2-6 carbon atoms is selected; and most preferably, alkenyl containing 2-5 carbon atoms is selected.

$C_1$-$C_{10}$ alkyl is alkyl having 1 to 10 carbon atoms, and can be a chain alkyl or a cycloalkyl; hydrogen on a ring of the cycloalkyl can be substituted by alkyl; a preferable lower limit of a number of carbon atoms of alkyl is 1, 2, 3, or 4; and a preferable upper limit of the number of carbon atoms of alkyl is 3, 4, 5, 6, or 8. Preferably, alkyl having 1-8 carbon atoms is selected; more preferably, a chain alkyl having 1-6 carbon atoms or a cycloalkyl having 3-8 carbon atoms is selected; and most preferably, a chain alkyl having 1-4 carbon atoms or a cycloalkyl having 5-7 carbon atoms is selected.

$C_2$-$C_{10}$ alkenyl is alkenyl having 2-10 carbon atoms, and can be a cyclic alkenyl or a chain alkenyl. The alkenyl preferably contains only one double-bond. A preferable lower limit of a number of carbon atoms of the alkenyl is 3, 4, or 5, and a preferable upper limit thereof is 3, 4, 5, 6, or 8. Preferably, alkenyl containing 2-10 carbon atoms is selected; more preferably, alkenyl containing 2-6 carbon atoms is selected; and most preferably, alkenyl containing 2-5 carbon atoms is selected.

Halogen is fluorine, chlorine, or bromine, and fluorine is preferable.

(Organic Solvent)

The organic solvent used in the electrolyte of the embodiments of the present disclosure can be preferably selected from the group consisting of cyclic carbonate, chain ester, lactone, ether, amide, and combinations thereof. In order to further improve the cycle performance at high temperature and high voltage and the storage performance at high temperature, the electrolyte preferably contains cyclic carbonate and chain carbonate.

The term "chain ester" used herein is a concept including both chain carbonate and chain carboxylic acid ester.

Examples of the cyclic carbonate include ethylene carbonate (abbreviated as EC), propylene carbonate (abbreviated as PC), etc.

Examples of the chain ester include: asymmetric chain carbonate, such as ethyl methyl carbonate (abbreviated as MEC), methyl propyl carbonate (abbreviated as MPC), methyl isopropyl carbonate (abbreviated as MIPC), methyl butyl carbonate, and ethyl propyl carbonate; symmetrical chain carbonate, such as dimethyl carbonate (abbreviated as DMC), diethyl carbonate (abbreviated as DEC), dipropyl carbonate, and dibutyl carbonate; and chain carboxylic acid ester, such as neovalerates (methyl neovalerate, ethyl neovalerate, propyl pivalate, etc.), methyl propionate, ethyl propionate, methyl acetate, and ethyl acetate.

Other suitable examples of the organic solvent may include: cyclic ester, such as tetrahydrofuran, 2-methyl tetrahydrofuran, 1, 4-dioxane, etc.; chain ester, such as 1, 2-dimethoxyethane, 1, 2-diethoxyethane, 1, 2-dibutoxyethane, etc.; amide, such as dimethylformamide; sulfone such as sulfolane; and lactones such as γ-butyrolactone, γ-valerolactone, and α-angelica lactone.

(Salt for Electrolyte)

The following lithium slats are suitable examples of the salt for electrolyte of the present disclosure.

(Li Salts-Type 1)

Suitable examples are complex salts of "Lewis Acid and LiF", such as $LiPF_6$, $LiBF_4$, $LiAsF_6$, $LiSbF_6$, $LiPF_4(CF3)_2$, $LiPF_3(C_2F_5)_3$, $LiPF_3(CF_3)_3$, $LiPF_3(iso-C_3F_7)_3$, and $LiPF_5$ (iso-$C_3F_7$). Preferable examples are $LiPF_6$, $LiBF_4$, and $LiAsF_6$. More preferable examples are $LiPF_6$ and $LiBF_4$.

(Li Salts-Type 2)

Suitable examples are "lithium imide salts or methylated lithium salts", such as $LiN(SO_2F)_2$, $LiN(SO_2CF_3)_2$, $LiN(SO_2C_2F_5)_2$, $(CF_2)_2(SO_2)_2NLi$ (cyclic), $(CF_2)_3(SO_2)_2NLi$ (cyclic), and $LiC(SO_2CF_3)_3$. Preferable examples are $LiN(SO_2F)_2$, $LiN(SO_2CF_3)_2$, and $LiN(SO_2C_2F_5)_2$. More preferable examples are $LiN(SO_2F)_2$ and $LiN(SO_2CF_3)_2$.

(Li Salts-Type 3)

Suitable examples are "lithium salts containing a $S(=O)_2O$ structure", such as $LiSO_3F$, $LiCF_3SO_3$, $CH_3SO_4Li$, $C_2H_5SO_4Li$, $C_3H_7SO_4Li$, lithium trifluoro (methanesulfonyloxy) borate (LiTFMSB), and lithium pentafluoro (methanesulfonyloxy) phosphate (LiPFMSP). Preferable examples are $LiSO_3F$, $CH_3SO_4Li$, $C_2H_5SO_4Li$, and LiTFMSB.

(Li Salts-Type 4)

Suitable examples are "lithium salts containing P=O or Cl=O", such as $LiPO_2F_2$, $Li_2PO_3F$, and $LiClO_4$. Preferable examples are $LiPO_2F_2$ and $Li_2PO_3F$.

(Li Slats-Type 5)

Suitable examples are "lithium salts with oxalate ligands as anions", such as lithium bis [oxalate-O,O'] borate (LiBOB), lithium difluoro[oxlate-O,O'] borate, lithium difluorobis[oxlate-O,O'] phosphate (LiPFO), and lithium tetrafluoro[oxalate-O,O'] phosphate. Preferable examples are LiBOB and LiPFO. One or more of these lithium salts can be used in the electrolyte.

The lithium salt is preferably selected from the group consisting of $LiPF_6$, $LiPO_2F_2$, $Li_2PO_3F$, $LiBF_4$, $LiSO_3F$, lithium trifluoro((methanesulfonyloxy) borate (LiTFMSB), $LiN(SO_2F)_2$, $LiN(SO_2CF_3)_2$, $LiN(SO_2C_2F_5)_2$, lithium bis [oxalate-O,O'] borate (LiBOB), lithium difluorobis [oxalate-O,O'] phosphate (LiPFO), lithium tetrafluoro[oxalte-O,O'] phosphate, and combinations thereof; more preferably, selected from the group consisting of $LiPF_6$, $LiBF_4$, $LiSO_3F$, lithium trifluoro((methanesulfonyloxy) borate (LiTFMSB), $LiPO_2F_2$, $LiN(SO_2CF_3)_2$, $LiN(SO_2F)_2$, lithium bis[oxalate-O,O'] borate (LiBOB), lithium difluorobis[oxalate-O,O'] phosphate (LiPFO), and combinations thereof; and most preferably, is $LiPF_6$.

(Preparation of Electrolyte)

The electrolytes according to the embodiments of the present disclosure can be obtained by a method as described below, for example, mixing the above organic solvents, then adding an electrolyte salt, the additive A, the additive B and the additive C.

(Synthesis of Multi-Cyano Six-Membered N-Heterocyclic Compounds)

(I) Preparation of Compounds Represented by Formula I-1:

A reaction equation of the synthesis of compounds represented by Formula I-1 is shown as below:

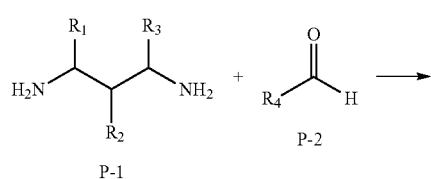

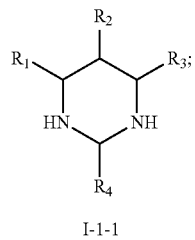

I-1-1

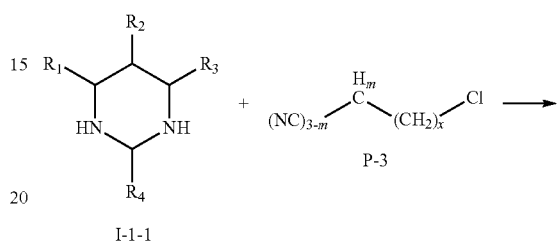

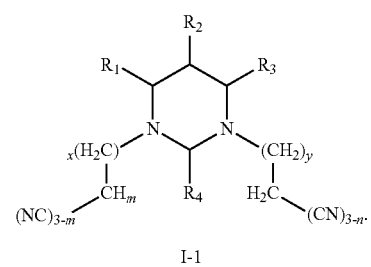

I-1

Specific steps of the preparation are as follow:

1. An aqueous solution of P-2 (concentration of 30-40%) was added dropwise to a raw material P-1 within 20-60 min while being stirred rapidly. After the dropwise addition was completed, the mixture was stirred rapidly for 15-30 h, and then refluxed and stirred for 3-5 h under temperature of 70-90° C. of oil bath. A colorless, fuming, and viscous liquid intermediate I-1-1 was obtained.

2. $K_2CO_3$, KI, and anhydrous acetonitrile were added subsequently, and stirred rapidly to form a solid-liquid mixture phase. A raw material P-3 was added quickly at 40-60° C., the mixture was further stirred for 10-20 h and then cooled to room temperature. A compound represented by Formula I-1 was obtained after separation and purification.

(II) Preparation of Compounds Represented by Formula I-2:

A reaction equation of the synthesis of compounds represented by Formula I-2 is shown as below:

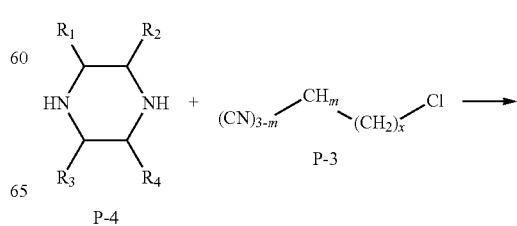

P-4

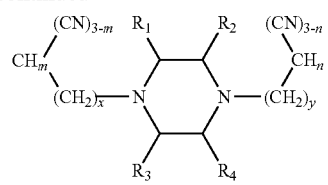

I-2

Specific steps of the preparation are as follow:

Anhydrous sodium carbonate, a raw material P-4 and a raw material P-3 were mixed in absolute ethanol, and were stirred to react for 2-5 h. The reaction mixture was washed for several times with hot ethanol to obtain a crude product, which was recrystallized to obtain a compound represented by Formula I-2.

(III) Preparation of Compounds Represented by Formula I-3:

A reaction equation of the synthesis of compounds represented by Formula I-3 is shown as below:

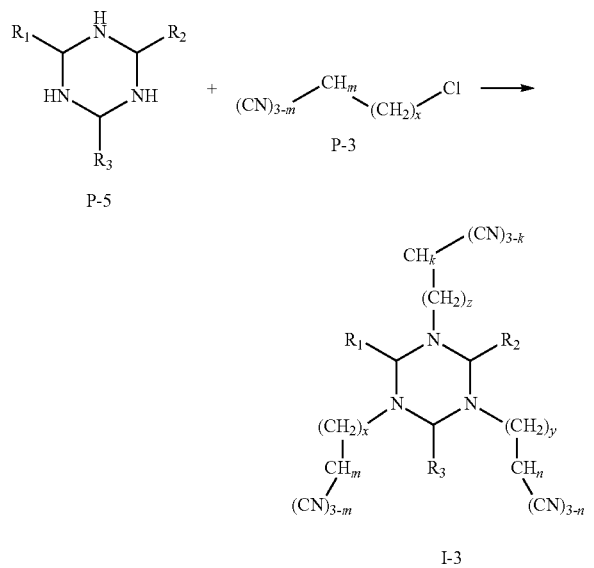

I-3

Specific steps of the preparation are as follow:

Anhydrous sodium carbonate, a raw material P-5 and a raw material P-3 were mixed in absolute ethanol and stirred to react for 2-5 h. The reaction mixture was washed for several times with hot ethanol to obtain a crude product, which was recrystallized to obtain a compound represented by Formula I-3.

Synthesis Example 1

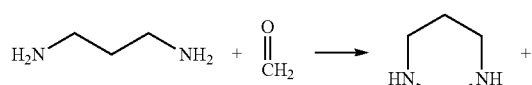

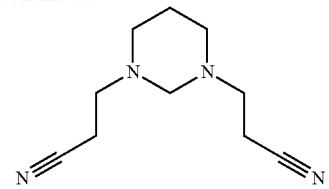

1. Aqueous solution of formaldehyde (37%) was added dropwise to 1,3-propanediamine within 0.5 h and stirred rapidly. After the dropwise addition was completed, the mixture was further stirred rapidly for 20 h, and refluxed and stirred at a temperature of 80° C. of oil bath for 4 h. A colorless, fuming and viscous liquid intermediate, hexahydropyrimidine, was obtained.

2. $K_2CO_3$, KI, and anhydrous acetonitrile were added subsequently. The mixture was stirred rapidly to form a solid-liquid mixture phase. β-chloropropionitrile was added within 0.5 h at a temperature of 60° C., then the reaction mixture was cooled to room temperature after being stirred for 17 h. A Compound A2 was obtained after separation and purification.

$^{13}$C-NMR of the Compound A2 is shown in FIG. 1.

Synthesis Example 2

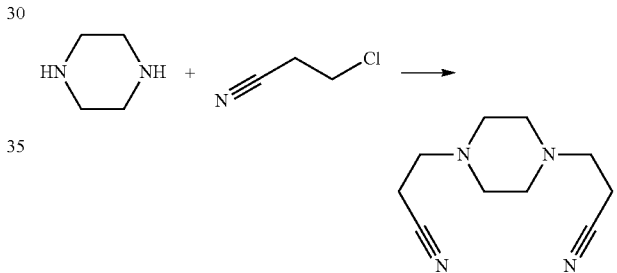

Anhydrous sodium carbonate, piperazine and β-chloropropionitrile were mixed in absolute ethanol, and stirred to react for 4 h. The reaction mixture was rinsed for several times with hot ethanol to obtain a crude product, which was recrystallized to obtain a Compound A8.

Figure 2:
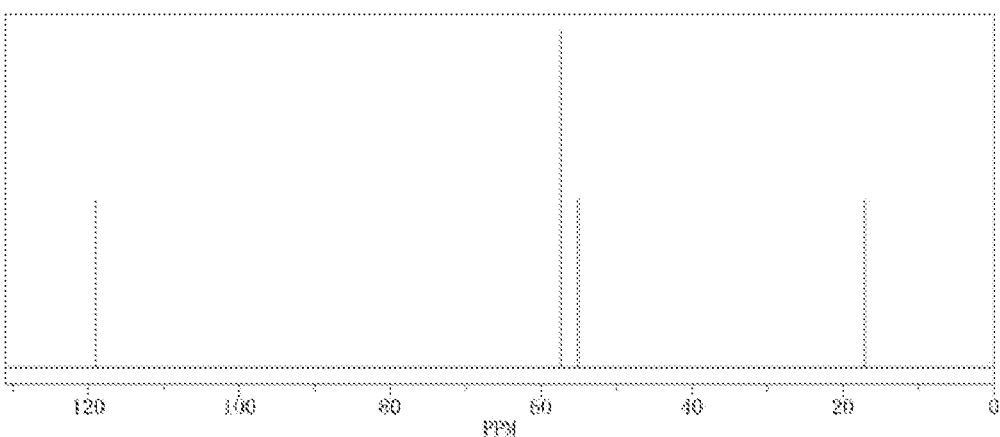
FIG. 2 is a nuclear magnetic resonance carbon spectrum of Compound A8.

$^{13}$C-NMR of the Compound A8 is shown in FIG. 2.

Synthesis Example 3

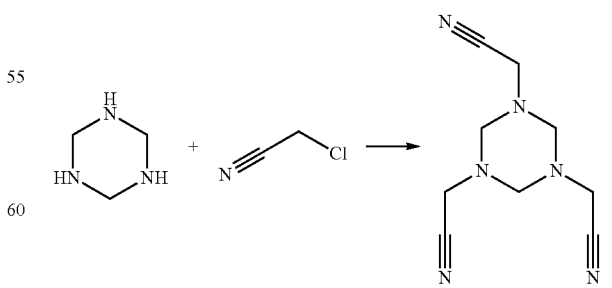

Anhydrous sodium carbonate, 1,3,5-s-triazine and chloroacetonitrile were mixed in absolute ethanol, and react for 4 h. The reaction mixture was rinsed for several times with hot ethanol to obtain a crude product, which was recrystallized to obtain a Compound A13.

Figure 3:
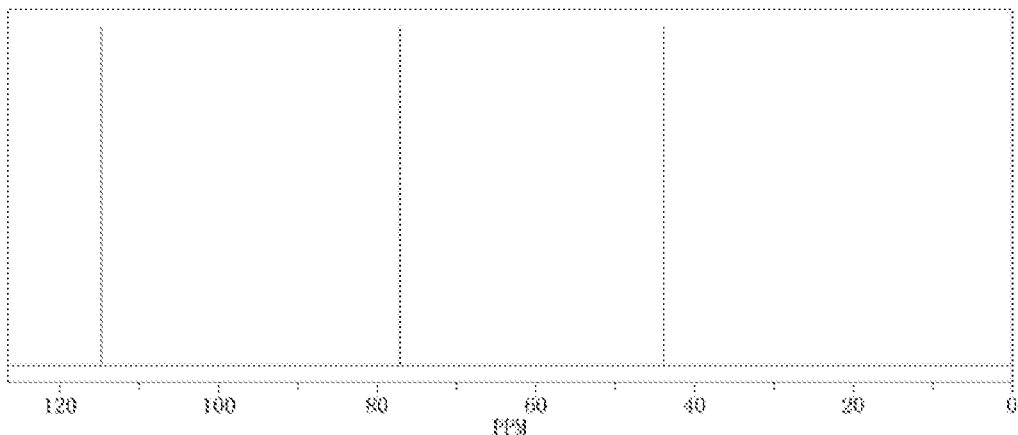
FIG. 3 is a nuclear magnetic resonance carbon spectrum of Compound A13.

$^{13}$C-NMR of the Compound A13 is shown in FIG. 3.

According to a second aspect of the present disclosure, a battery is described below.

The electrochemical device according to the embodiments of the present disclosure includes a positive electrode plate, a negative electrode plate, a separator disposed between the positive electrode plate and the negative electrode plate, and an electrolyte. It should be noted that the battery according to the embodiments of the present disclosure can be a lithium-ion secondary battery, a lithium primary battery or a lithium-ion capacitor.

When the electrochemical device is a lithium-ion secondary battery, the positive electrode plate thereof includes a positive electrode active material capable of de-intercalating and intercalating lithium ions, and the negative electrode plate thereof includes a negative electrode active material capable of intercalating and de-intercalating lithium ions.

Specifically, when the electrochemical device is a lithium-ion secondary battery, the positive electrode active material can be selected from the group consisting of lithium cobalt oxide, lithium nickel oxide, lithium manganese oxide, lithium nickel manganese oxide, lithium nickel cobalt manganese oxide, lithium nickel cobalt aluminum oxide, a compound formed by doping a transition metal or a non-transition metal into the lithium transition metal oxides, and combinations thereof. The positive electrode active material can be a layered lithium-containing oxide, a spinel-type lithium-containing oxide, an olivine-type lithium-containing phosphate compound or the like. However, the positive electrode active material is not limited to the above materials. Any conventional material that can be used as a positive electrode active material of a lithium-ion battery can be adopted. These positive electrode active materials can be used individually or in combination. The negative electrode active material can be soft carbon, hard carbon, artificial graphite, natural graphite, silicon, silicon oxide, silicon carbon composite, lithium titanate, metal capable of forming an alloy with lithium, or the like. Specifically, a carbon-based negative electrode, a silicon-based negative electrode, a tin-based negative electrode, or the like can be used. However, the negative electrode active material is not limited to these materials. Any conventional material that can be used as a negative electrode active material of a lithium-ion battery can be adopted. These negative electrode active materials can be used individually or in combination.

Specifically, when the electrochemical device is a lithium primary battery, the negative electrode material of the lithium primary battery is lithium metal or lithium alloy; the the common positive electrode active materials of the lithium primary battery include: solid halide such as copper fluoride (CuF$_2$), copper chloride (CuCl$_2$), silver chloride (AgCl), polyfluorocarbon ((CF)$_4$), solid sulfide such as copper sulfide (CuS), iron sulfide (FeS), iron disulfide (FeS$_2$), solid oxide such as manganese dioxide (MnO$_2$), copper oxide (CuO), molybdenum trioxide (MoO$_3$), vanadium pentoxide (V$_2$O$_5$), solid oxyacid salts such as silver chromate (Ag$_2$CrO$_4$) and lead citrate (Pb$_2$Bi$_2$O$_5$).

When the electrochemical device is a lithium-ion capacitor, the negative electrode material of the lithium-ion capacitor is graphite or a polyacene material, and the positive electrode material thereof is activated carbon.

In the above-mentioned electrochemical device, the separator is not specifically limited, and can be any separator material used in the existing batteries, such as polyethylene, polypropylene, polyvinylidene fluoride, and a multilayered composite film thereof, but is not limited thereto.

The electrolyte is the electrolyte according to the first aspect of the present disclosure.

In the above-mentioned electrochemical device, the positive electrode plate further includes a binder and a conductive agent. A positive electrode slurry containing the positive electrode active material, the binder and the conductive agent is coated on a positive current collector and then dried to obtain the positive electrode plate. Similarly, a negative electrode slurry containing the negative electrode active material, a binder and a conductive agent is coated on a negative current collector, and then dried to obtain the negative electrode plate.

Further, when the electrochemical device is a lithium-ion secondary battery, a charging cutoff voltage of the electrochemical device according to the embodiments of the present disclosure is not less than 4.2V. That is, the battery can operate in a range of 4.2V to 4.9V, and further optionally in a range of 4.3V to 4.8V. In a high voltage state, the higher the valence state of the surface transition metal of the positive electrode material, the stronger the coulomb interaction of the cynao groups in the additive, i.e., the stronger the protective effect the additive can provide.

EXAMPLES

The following specific examples of the present disclosure merely illustrate the embodiments of the lithium-ion secondary battery (also referred as to lithium-ion battery hereinafter), but the present disclosure is not limited thereto. The present disclosure is described in detail in combination with the examples of the lithium-ion secondary battery. It should be understood that these examples are merely used to illustrate the present disclosure, but not intended to limit the scope of the present disclosure. The reagents, materials and instruments used in the following examples and comparative examples are commercially available, unless otherwise specified.

Preparation of Electrolyte: A mixture of ethylene carbonate (EC), ethyl methyl carbonate (EMC) and diethyl carbonate (DEC) was used as solvent, in which a mass ratio of EC, EMC and DEC is 1:1:1. LiPF$_6$ was used as the lithium salt, and a total content of LiPF$_6$ is 12.5% of a total weight of the electrolyte. The additive is added to the composition of the electrolyte shown in Table 1 is added, in which the concentrations of the additive are ratios of the weight of the additive to the total weight of the electrolyte.

The used additives are shown as below:

Additive A:

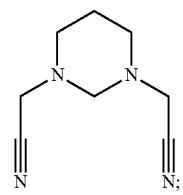

A1

Additive B:

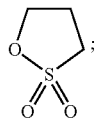

(PS)

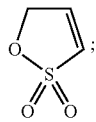

(PES)

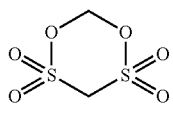

(MMDS)

Additive C:

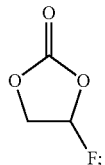

(FEC)

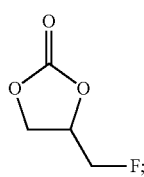

(FPC)

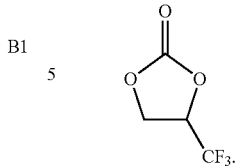

(TFPC)

Preparation of Positive Electrode Plate: $LiCoO_2$ used as the positive electrode active material, PVDF used as the binder, and acetylene black used as the conductive agent were mixed in a mass ratio of 98:1:1, and then N-methylpyrrolidone was added. The mixture was stirred with a vacuum mixer until a stable and uniform positive electrode slurry was obtained. The positive electrode slurry was uniformly coated on an aluminum foil. The aluminum foil was dried in the air at room temperature, transferred to a blast oven and dried there at 120° C. for 1 h, following by cold pressing and cutting, so as to obtain a positive electrode plate.

Preparation of Negative Electrode Plate: Graphite used as the negative electrode active material, acetylene black used as the conductive agent, carboxymethyl cellulose sodium (CMC) solution used as a thickener, and styrene-butadiene rubber emulsion used as the binder were mixed in a mass ratio of 97:1:1:1, and then deionized water was then added. The mixture was stirred with a vacuum mixer until a stable and uniform negative electrode slurry was obtained. The negative electrode slurry was uniformly coated on a copper foil. The copper foil was dried in the air at room temperature, transferred to a blast oven and dried there at 120° C. for 1 h, following by cold pressing and cutting, so as to obtain a negative electrode plate.

Preparation of Battery: The positive electrode plate, the negative electrode plate and a PP/PE/PP separator were wound to obtain a cell. After the cell had been placed in a package shell, the electrolyte was injected, and the package shell was sealed. Through subsequent procedures such as storing, hot and cold pressing, formation, air exhausting, capacitance test, a lithium-ion battery was obtained.

In Table 1, the concentrations of the additive A, the additive B and the additive C are in percentages by weight based on a total weight of the electrolyte.

TABLE 1

Components and proportion of components in the electrolytes of Batteries 1-28 and Comparative Batteries

| No. | solvent | Additive A type | conc. | Additive B type | conc. | Additive C type | conc. |
|---|---|---|---|---|---|---|---|
| Battery 1 | EC:EMC:DEC = 1:1:1 | A1 | 0.001% | B1 | 3.0% | C1 | 2.0% |
| Battery 2 | EC:EMC:DEC = 1:1:1 | A1 | 0.01% | B1 | 3.0% | C1 | 2.0% |
| Battery 3 | EC:EMC:DEC = 1:1:1 | A1 | 0.1% | B1 | 3.0% | C1 | 2.0% |
| Battery 4 | EC:EMC:DEC = 1:1:1 | A1 | 1.0% | B1 | 3.0% | C1 | 2.0% |
| Battery 5 | EC:EMC:DEC = 1:1:1 | A1 | 2.0% | B1 | 3.0% | C1 | 2.0% |
| Battery 6 | EC:EMC:DEC = 1:1:1 | A1 | 3.5% | B1 | 3.0% | C1 | 2.0% |
| Battery 7 | EC:EMC:DEC = 1:1:1 | A1 | 6.0% | B1 | 3.0% | C1 | 2.0% |
| Battery 8 | EC:EMC:DEC = 1:1:1 | A1 | 8.0% | B1 | 3.0% | C1 | 2.0% |
| Battery 9 | EC:EMC:DEC = 1:1:1 | A1 | 10.0% | B1 | 3.0% | C1 | 2.0% |
| Battery 10 | EC:EMC:DEC = 1:1:1 | A1 | 2.0% | B1 | 0.1% | C1 | 2.0% |
| Battery 11 | EC:EMC:DEC = 1:1:1 | A1 | 2.0% | B1 | 0.5% | C1 | 2.0% |
| Battery 12 | EC:EMC:DEC = 1:1:1 | A1 | 2.0% | B1 | 1.0% | C1 | 2.0% |
| Battery 13 | EC:EMC:DEC = 1:1:1 | A1 | 2.0% | B1 | 2.0% | C1 | 2.0% |
| Battery 14 | EC:EMC:DEC = 1:1:1 | A1 | 2.0% | B2 | 3.0% | C1 | 2.0% |
| Battery 15 | EC:EMC:DEC = 1:1:1 | A1 | 2.0% | B3 | 3.0% | C1 | 2.0% |

TABLE 1-continued

Components and proportion of components in the electrolytes of Batteries 1-28 and Comparative Batteries

| No. | solvent | Additive A type | Additive A conc. | Additive B type | Additive B conc. | Additive C type | Additive C conc. |
|---|---|---|---|---|---|---|---|
| Battery 16 | EC:EMC:DEC = 1:1:1 | A1 | 2.0% | B1 | 6.0% | C1 | 2.0% |
| Battery 17 | EC:EMC:DEC = 1:1:1 | A1 | 2.0% | B1 | 10.0% | C1 | 2.0% |
| Battery 18 | EC:EMC:DEC = 1:1:1 | A1 | 2.0% | B1 | 3.0% | C1 | 0.1% |
| Battery 19 | EC:EMC:DEC = 1:1:1 | A1 | 2.0% | B1 | 3.0% | C1 | 1.0% |
| Battery 20 | EC:EMC:DEC = 1:1:1 | A1 | 2.0% | B1 | 3.0% | C1 | 3.0% |
| Battery 21 | EC:EMC:DEC = 1:1:1 | A1 | 2.0% | B1 | 3.0% | C1 | 6.0% |
| Battery 22 | EC:EMC:DEC = 1:1:1 | A1 | 2.0% | B1 | 3.0% | C1 | 10.0% |
| Battery 23 | EC:EMC:DEC = 1:1:1 | A1 | 2.0% | B1 | 3.0% | C2 | 2.0% |
| Battery 24 | EC:EMC:DEC = 1:1:1 | A1 | 2.0% | B2 | 3.0% | C2 | 2.0% |
| Battery 25 | EC:EMC:DEC = 1:1:1 | A1 | 2.0% | B3 | 3.0% | C2 | 2.0% |
| Battery 26 | EC:EMC:DEC = 1:1:1 | A1 | 2.0% | B1 | 3.0% | C3 | 2.0% |
| Battery 27 | EC:EMC:DEC = 1:1:1 | A1 | 2.0% | B2 | 3.0% | C3 | 2.0% |
| Battery 28 | EC:EMC:DEC = 1:1:1 | A1 | 2.0% | B3 | 3.0% | C3 | 2.0% |
| Comparative Battery 1 | EC:EMC:DEC = 1:1:1 | / | / | / | / | / | / |
| Comparative Battery 2 | EC:EMC:DEC = 1:1:1 | A1 | 2% | / | / | / | / |
| Comparative Battery 3 | EC:EMC:DEC = 1:1:1 | A1 | 2% | B3 | 3.0% | / | / |
| Comparative Battery 24 | EC:EMC:DEC = 1:1:1 | A1 | 2% | / | / | C1 | 2.0% |

In Table 1, "/" means the additive is absent.

The high-voltage and high-temperature cycle performance of the lithium-ion batteries was evaluated by means of the cycle capacitance retention rate, and the high-temperature storage performance was evaluated by means of the thickness expansion ratio of the lithium-ion batteries. The Batteries 1-28 were tested as follows:

(1) Cycle Performance Test of Lithium-Ion Batteries at High Voltage

At 25° C., the lithium-ion secondary battery was firstly charged with a constant current of 1 C to a voltage of 4.35 V, further charged at a constant voltage of 4.35 V until the current was 0.05 C, and then discharged at a constant current of 1 C to a voltage of 3.0 V. This procedure is called as one charge and discharge cycle, and a discharge capacitance during this first cycle was referred to as a discharge capacitance of the $1^{st}$ cycle. The lithium-ion battery was subjected to 200 charge and discharge cycles according to the above procedure, and the discharge capacitance of the $200^{th}$ cycle was measured.

Capacitance retention rate (%) of the lithium-ion battery after 200 cycles=(discharge capacitance of the lithium-ion battery in the $200^{th}$ cycle/ discharge capacity of the lithium-ion battery in the $1^{st}$ cycle)×100%.

(2) Cycle Performance Test of Lithium-Ion Batteries at High Temperature and High Voltage At 45° C., the lithium-ion battery was firstly charged with a constant current of 1 C to a voltage of 4.35 V, further charged at a constant voltage of 4.35 V until the current was 0.05 C, and then discharged at a constant current of 1 C to a voltage of 3.0 V. This procedure was called as one charge and discharge cycle, and a discharge capacitance during this first cycle was referred to as a discharge capacitance of the $1^{st}$ cycle. The lithium-ion battery was subjected to 200 charge and discharge cycles according to the above procedure, and the discharge capacitance of the $200^{th}$ cycle was measured.

Capacitance retention rate (%) of the lithium-ion battery after 200 cycles=(discharge capacitance of the lithium-ion battery in the $200^{th}$ cycle/ discharge capacity of the lithium-ion battery in the $1^{st}$ cycle)×100%.

(3) Storage Performance Test of Lithium-Ion Batteries at High Temperature

At 85° C., the lithium-ion battery was charged with a constant current of 0.5 C to a voltage of 4.35 V, and then charged at a constant voltage of 4.35 V until the current was 0.05 C; at this time, the thickness of the lithium-ion battery was measured and recorded as h0. The lithium-ion battery was then placed in an incubator at 85° C., stored for 24 hours and then taken out; at this time, the thickness of the lithium-ion battery was measured and recorded as h1.

Thickness expansion ratio of the lithium-ion battery after 24h storage (%)=[(h1−h0)/h0]×100%.

TABLE 2

Test results of cycle capacitance retention rate and thickness expansion ratio

| No. | 25° C./4.35 V/ capacitance retention rate after 200 cycles | 45° C./4.35 V/ capacitance retention rate after 200 cycles | thickness expansion ratio after 24 h storage at 85° C. |
|---|---|---|---|
| Battery 1 | 89% | 86% | 13% |
| Battery 2 | 91% | 88% | 10% |
| Battery 3 | 93% | 90% | 8% |
| Battery 4 | 95% | 94% | 4% |
| Battery 5 | 99% | 98% | 2% |
| Battery 6 | 98% | 96% | 2% |
| Battery 7 | 95% | 94% | 2% |
| Battery 8 | 93% | 90% | 2% |
| Battery 9 | 90% | 86% | 1% |
| Battery 10 | 96% | 93% | 6% |
| Battery 11 | 97% | 94% | 5% |
| Battery 12 | 98% | 96% | 4% |
| Battery 13 | 99% | 96% | 3% |
| Battery 14 | 99% | 98% | 2% |
| Battery 15 | 99% | 98% | 2% |
| Battery 16 | 96% | 95% | 2% |
| Battery 17 | 94% | 91% | 1% |

TABLE 2-continued

Test results of cycle capacitance retention rate and thickness expansion ratio

| No. | 25° C./4.35 V/ capacitance retention rate after 200 cycles | 45° C./4.35 V/ capacitance retention rate after 200 cycles | thickness expansion ratio after 24 h storage at 85° C. |
| --- | --- | --- | --- |
| Battery 18 | 98% | 96% | 3% |
| Battery 19 | 99% | 98% | 2% |
| Battery 20 | 96% | 96% | 2% |
| Battery 21 | 91% | 89% | 1% |
| Battery 22 | 86% | 84% | 2% |
| Battery 23 | 98% | 96% | 3% |
| Battery 24 | 98% | 97% | 2% |
| Battery 25 | 97% | 96% | 2% |
| Battery 26 | 98% | 96% | 3% |
| Battery 27 | 97% | 96% | 3% |
| Battery 28 | 97% | 95% | 2% |
| Comparative Battery 1 | 83% | 75% | 67% |
| Comparative Battery 2 | 94% | 91% | 7% |
| Comparative Battery 3 | 98% | 96% | 5% |
| Comparative Battery 4 | 97% | 95% | 6% |

Comparing Batteries 1-28 with Comparative Battery 1, it can be seen that the combination of additives added in the electrolyte of the lithium-ion batteries can significantly improve the cycle performance at high voltage and high temperature, and the storage performance at high temperature of the lithium-ion batteries.

It can be seen from Batteries 1-9 that when the charge cut-off voltage is 4.35V, the cycle capacitance retention rates of the battery at 25° C. and 45° C. reached an optimal value and then had a dropping trend, while battery expansion rate after 24 h storage at 85° C. kept decreasing, with the increase of the amount of the additive A (0.001% to 10%).

The reason lies in that the multi-cyano six-membered N-heterocyclic compound molecule in the additive A contains two or more cynao groups at the same time, the nitrogen atoms in these cynao groups contain lone pair electrons, which can be strongly complexed with the 3d empty orbit of the surface transition metal of the positive electrode material. In this way, the surface activity of the positive electrode plate is reduced, while the surface of the positive electrode plate (especially at high SOC) is prevented from directly contacting the electrolyte. Therefore, side reaction at the surface of the positive electrode plate is significantly reduced, and thus less lithium ions are consumed in the side reaction, i.e., the consumption rate of the reversible lithium ions is greatly reduced, which results in a significantly enhanced cycle capacitance retention rate. In addition, since part of the side reactions on surface can generate gas, the reduction of surface side reactions means a decrease in gas production, and thus the thickness expansion effect of the battery at high temperature is significantly alleviated.

The cynao group in the additive A can be complexed with both $Li^+$ and the transition metals on the surface of the positive electrode material. Therefore, when the addition amount of the additive A is excessively great, on the one hand, the excessive additive A (except that adsorbed on the surface of the LCO) would consume $Li^+$, resulting in a decrease in the circulating $Li^+$ in the battery cell, and on the other hand, it would lead to an increase in the overall viscosity of the electrolyte and a decrease in the ionic conductivity, thereby reducing the cycle capacitance retention rate of the battery cell. When the addition amount of the additive A is too small, the effect would be not significant.

By comparing with Comparative Battery 2, Comparative Battery 3 and Comparative Battery 4, it can be seen that addition of the additive A, the additive B and the additive C can effectively reduce the expansion ratio of the battery after storage at 85° C., and effectively improve the cycle performance at 25° C. and 45° C.

The additive B can further improve the cycle performance at high temperature and high voltage and the storage performance at high temperature of the lithium-ion battery, and further reduce the gas production. The reason lies in that, the additive A can stabilize the positive electrode surface and reduce the side reactions on the positive electrode surface, while the additive B can be preferentially reduced on the graphite electrode surface due to its relatively high reduction potential and sulfur element-containing molecules in the reduction product are adsorbed on catalytically active sites of the graphite surface to form a more stable SEI film, so as to effectively reducing the reductive decomposition of the electrolyte and reducing the side reactions. Thus, the synergic effect of the additive A and the additive B further enhances the performance of the lithium-ion battery. The main mechanism of the effect of the additive C is in that the halogenated cyclic carbonate is a good film forming additive, which can preferentially form a film on the anode than other substances in the electrolyte, thereby preventing damage from the solvent and solvated lithium ions to the graphite structure. However, if the addition amount is too large, the impedance of the positive electrode will be increased. When the addition amount of the additive C added is small, the improvement of the performance is not significant, because the amount of the additive C participating in the film formation is excessively small, and the additive C can hardly play a significant role. When the additive C is added too much, the formed SEI film will be too thick, which will, on the one hand, reduce the migration velocity of lithium ions, increase battery impedance and even lead to lithium precipitation; and on the other hand, excessive film-forming reaction consumes a large number of lithium ions, significantly increasing the irreversible capacitance and deteriorating the battery performance. When the content of the additive C is 4%, optimal electrochemical performances such as high/low temperature cycle performance, high-temperature storage performance and gas production, were obtained.

In summary, when the addition amounts of the additive A, the additive B and the additive C are 2%, 3% and 2%, respectively, an optimal synergistic effect was obtained.

OTHER EXAMPLES

Other lithium ion batteries were prepared with the method of the above examples, and the compositions of the electrolytes are shown in Table 3.

In Table 3, the concentrations of the additive A, the additive B and the additive C are percentage by weight based on the total weight of the electrolyte.

TABLE 3

Components and proportion of components in the electrolytes of Batteries 29-45

| No. | solvent | Additive A type | conc. | Additive B type | conc. | Additive C type | conc. |
|---|---|---|---|---|---|---|---|
| Battery 29 | EC:EMC:DEC = 1:1:1 | A2 | 2.0% | B1 | 3.0% | C1 | 2.0% |
| Battery 30 | EC:EMC:DEC = 1:1:1 | A3 | 2.0% | B2 | 3.0% | C2 | 2.0% |
| Battery 31 | EC:EMC:DEC = 1:1:1 | A4 | 2.0% | B3 | 3.0% | C3 | 2.0% |
| Battery 32 | EC:EMC:DEC = 1:1:1 | A5 | 2.0% | B2 | 3.0% | C2 | 2.0% |
| Battery 33 | EC:EMC:DEC = 1:1:1 | A6 | 2.0% | B1 | 3.0% | C1 | 2.0% |
| Battery 34 | EC:EMC:DEC = 1:1:1 | A7 | 2.0% | B2 | 3.0% | C2 | 2.0% |
| Battery 35 | EC:EMC:DEC = 1:1:1 | A8 | 2.0% | B1 | 3.0% | C1 | 2.0% |
| Battery 36 | EC:EMC:DEC = 1:1:1 | A9 | 2.0% | B2 | 3.0% | C2 | 2.0% |
| Battery 37 | EC:EMC:DEC = 1:1:1 | A10 | 2.0% | B1 | 3.0% | C3 | 2.0% |
| Battery 38 | EC:EMC:DEC = 1:1:1 | A11 | 2.0% | B3 | 3.0% | C2 | 2.0% |
| Battery 39 | EC:EMC:DEC = 1:1:1 | A12 | 2.0% | B1 | 3.0% | C1 | 2.0% |
| Battery 40 | EC:EMC:DEC = 1:1:1 | A13 | 2.0% | B2 | 3.0% | C3 | 2.0% |
| Battery 41 | EC:EMC:DEC = 1:1:1 | A14 | 2.0% | B1 | 3.0% | C1 | 2.0% |
| Battery 42 | EC:EMC:DEC = 1:1:1 | A15 | 2.0% | B3 | 3.0% | C2 | 2.0% |
| Battery 43 | EC:EMC:DEC = 1:1:1 | A16 | 2.0% | B1 | 3.0% | C3 | 2.0% |
| Battery 44 | EC:EMC:DEC = 1:1:1 | A17 | 2.0% | B2 | 3.0% | C2 | 2.0% |
| Battery 45 | EC:EMC:DEC = 1:1:1 | A18 | 2.0% | B3 | 3.0% | C1 | 2.0% |

The cycle performance at high voltage and high temperature and the storage performance at high temperature of Batteries 29-45 using the electrolytes shown in Table 3 are similar to those of Batteries 5, 14 and 15, and will not be described in details herein.

According to the disclosure and teachings of the foregoing description, those skilled in the art can also make appropriate changes and modifications to the embodiments described above. Therefore, the present disclosure is not limited to the specific embodiments disclosed and described above, and some modifications and variations shall fall within the protection scope of the claims. In addition, although some specific terms used in the specification are merely for convenience of description and do not constitute any limitation.

What is claimed is:

1. An electrolyte, comprising an additive A, an additive B and an additive C, wherein the additive A is selected from a group consisting of multi-cyano six-membered N-heterocyclic compounds represented by Formula I-1, Formula I-3, and combinations thereof:

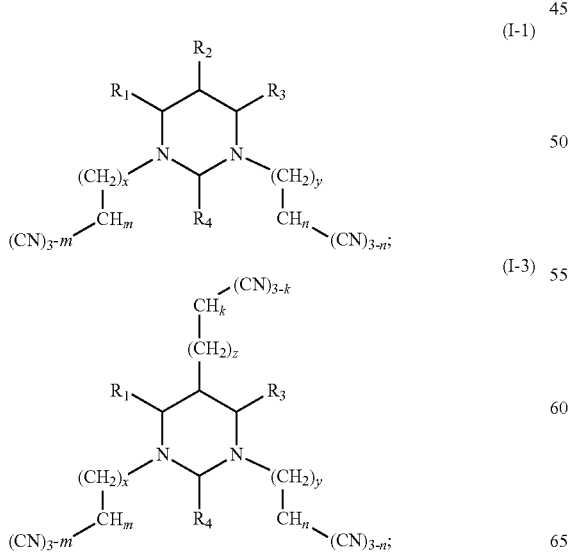

wherein $R_1$, $R_2$, $R_3$ and $R_4$ are each independently selected from a group consisting of hydrogen, halogen, substituted or unsubstituted $C_1$-$C_{12}$ alkyl, substituted or unsubstituted $C_1$-$C_{12}$ alkoxy, substituted or unsubstituted $C_1$-$C_{12}$ amine group, substituted or unsubstituted $C_1$-$C_{12}$ alkenyl, substituted or unsubstituted $C_2$-$C_{12}$ alkynyl, substituted or unsubstituted $C_6$-$C_{26}$ aryl, and substituted or unsubstituted $C_4$-$C_{12}$ heterocyclic group; the substituent for the above groups, if present, is independently selected from a group consisting of halogen, cyano, $C_1$-$C_6$ alkyl, $C_2$-$C_6$ alkenyl, $C_1$-$C_6$ alkoxy, and combinations thereof; x, y and z are each an integer independently selected from 0-8; and m, n and k are each an integer independently selected from 0-2; preferably, m, n and k are each independently 1 or 2; wherein the additive B is at least one sulfonate compound selected from a group consisting of a sultone compound, a disulfonate compound, and combinations thereof; and wherein the additive C is at least one halogenated cyclic carbonate compound, and wherein the additives A and B are independently are from 0.001% to 10% by weight of the electrolyte.

2. The electrolyte according to claim 1, wherein
$R_1$, $R_2$, $R_3$ and $R_4$ are each independently selected from a group consisting of hydrogen, halogen, substituted or unsubstituted $C_1$-$C_3$ linear or branched alkyl, substituted or unsubstituted $C_5$-$C_7$ cycloalkyl, substituted or unsubstituted $C_1$-$C_3$ alkoxy, substituted or unsubstituted $C_1$-$C_3$ amine group, substituted or unsubstituted $C_2$-$C_3$ alkenyl, substituted or unsubstituted $C_2$-$C_3$ alkynyl, substituted or unsubstituted $C_6$-$C_8$ aryl, and substituted or unsubstituted $C_4$-$C_7$ heterocyclic group, wherein the substituent for the above groups, if present, is halogen.

3. The electrolyte according to claim 1, wherein
in Formula I-1, $R_1$ and $R_3$ are identical, and preferably, $R_1$, $R_3$ and $R_4$ are identical; and
in Formula I-3, at least two of $R_1$, $R_2$ and $R_3$ are identical.

4. The electrolyte according to claim 3, wherein
in Formula I-1, $R_1$ and $R_3$ are hydrogen; and preferably, $R_1$, $R_3$ and $R_4$ are hydrogen; and
in Formula I-3, at least two of $R_1$, $R_2$ and $R_3$ are hydrogen.

5. The electrolyte according to claim 1, wherein the multi-cyano six-membered N-heterocyclic compound represented by Formula I-1 is selected from a group consisting of the following compounds and combinations thereof:

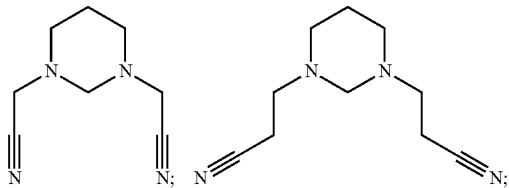

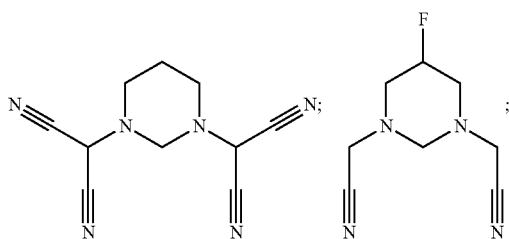

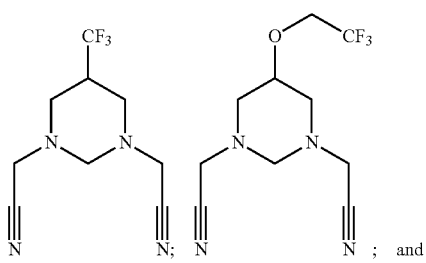 and

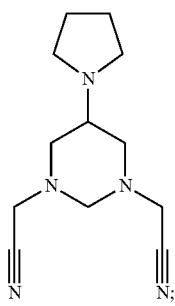

the multi-cyano six-membered N-heterocyclic compound represented by Formula I-3 is selected from a group consisting of the following compounds and combinations thereof:

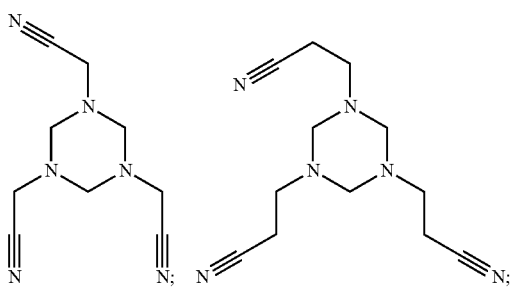

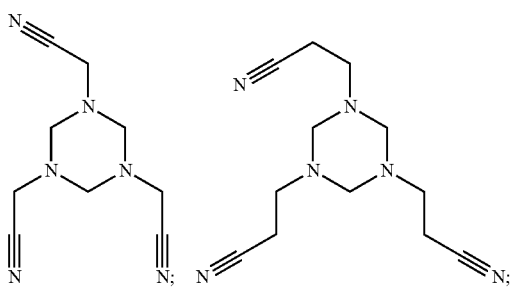

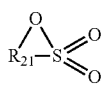

6. The electrolyte according to claim 1,
   wherein the sultone compound is selected from a group consisting of compounds represented by Formula II-1, and combinations thereof, $$\text{(II-1)}$$

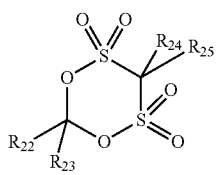

wherein $R_{21}$ is selected from substituted or unsubstituted $C_1$-$C_6$ alkylene, and substituted or unsubstituted $C_2$-$C_6$ alkenylene, wherein the substituent for the above groups, if present, is halogen, $C_1$-$C_3$ alkyl, or $C_2$-$C_4$ alkenyl; and wherein the disulfonate compound is selected from a group consisting of compounds represented by Formula II-2, and combinations thereof, (II-2)

wherein $R_{22}$, $R_{23}$, $R_{24}$ and $R_{25}$ are each independently selected from hydrogen, halogen, substituted or unsubstituted $C_1$-$C_{10}$ alkyl, and substituted or unsubstituted $C_2$-$C_{10}$ alkenyl, wherein the substituent for the above groups, if present, is halogen, $C_1$-$C_3$ alkyl, or $C_2$-$C_4$ alkenyl.

7. The electrolyte according to claim 1, wherein the at least one halogenated cyclic carbonate compound is selected from a group consisting of compounds represented by Formula III, and combinations thereof:

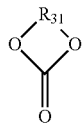

(III)

wherein $R_{31}$ is selected from alkenyl-substituted $C_1$-$C_6$ alkylene, and substituted or unsubstituted $C_2$-$C_6$ alkenylene, wherein the substituent for the above groups, if present, is selected from a group consisting of halogen, $C_1$-$C_6$ alkyl, $C_2$-$C_6$ alkenyl, and combinations thereof.

8. The electrolyte according to claim 1, wherein the additive C is from 0.1% to 10%, by weight of the electrolyte.

9. An electrochemical device, comprising a positive electrode plate, a negative electrode plate, a separator positioned between the positive electrode plate and the negative electrode plate, and an electrolyte according to claim 1.

10. The electrochemical device according to claim 9, wherein the electrochemical device is a lithium-ion secondary battery, a lithium primary battery, or a lithium-ion capacitor.

11. The electrochemical device according to claim 9, wherein the electrochemical device is a lithium-ion secondary battery, and the lithium-ion secondary battery has a charge cut-off voltage no less than 4.2V.

12. The electrolyte according to claim 1, wherein the additive A is from 0.01% to 6%, by weight of the electrolyte.

13. The electrolyte according to claim 1, wherein the additive A is from 0.1% to 3.5%, by weight of the electrolyte.

14. The electrolyte according to claim 1, wherein the additive B is from 0.5% to 7%, by weight of the electrolyte.

15. The electrolyte according to claim 1, wherein the additive B is from 1% to 4%, by weight of the electrolyte.

16. The electrolyte according to claim 1, wherein the additive C is from 0.5% to 5%, by weight of the electrolyte.

17. The electrolyte according to claim 1, wherein the additive C is from 1% to 4%, by weight of the electrolyte.

* * * * *